(12) United States Patent
Karup et al.

(10) Patent No.: US 11,112,399 B2
(45) Date of Patent: Sep. 7, 2021

(54) APPARATUS AND A METHOD FOR ANALYZING A BODY FLUID SAMPLE FROM A SAMPLER

(71) Applicant: Radiometer Medical ApS, Brønshøj (DK)

(72) Inventors: Kasper Karup, Copenhagen (DK); Frederik Bundgaard, Copenhagen (DK); Kristian Hvidtfeldt, Copenhagen (DK); Nina Pytter Laursen, Copenhagen (DK)

(73) Assignee: RADIOMETER MEDICAL APS, Bronshoj (DK)

( * ) Notice: Subject to any disclaimer, the term of this patent is extended or adjusted under 35 U.S.C. 154(b) by 210 days.

(21) Appl. No.: 16/471,073

(22) PCT Filed: Dec. 4, 2017

(86) PCT No.: PCT/EP2017/081316
§ 371 (c)(1),
(2) Date: Jun. 19, 2019

(87) PCT Pub. No.: WO2018/114295
PCT Pub. Date: Jun. 28, 2018

(65) Prior Publication Data
US 2019/0360999 A1    Nov. 28, 2019

(30) Foreign Application Priority Data
Dec. 23, 2016  (DK) .......................... PA 2016 00791

(51) Int. Cl.
*G01N 33/487*     (2006.01)
*G01N 33/49*      (2006.01)
(Continued)

(52) U.S. Cl.
CPC .... *G01N 33/48792* (2013.01); *G01N 33/4925* (2013.01); *G01N 35/00732* (2013.01);
(Continued)

(58) Field of Classification Search
CPC ......... G01N 33/48792; G01N 35/1009; G01N 33/4925; G01N 35/00732; G01N 35/02; G16H 10/40
See application file for complete search history.

(56) References Cited

U.S. PATENT DOCUMENTS

| 5,684,969 A | * | 11/1997 | Ishida ................... | G06F 3/0489 345/660 |
| 5,796,403 A | * | 8/1998 | Adams ..................... | G09G 5/14 715/803 |

(Continued)

FOREIGN PATENT DOCUMENTS

| CN | 101169407 A | 4/2008 |
| CN | 104297508 A | 1/2015 |

(Continued)

OTHER PUBLICATIONS

International Search Report for International Application No. PCT/EP2017/081316, dated Jan. 29, 2019 (three pages).
(Continued)

*Primary Examiner* — Shogo Sasaki
(74) *Attorney, Agent, or Firm* — Finnegan, Henderson, Farabow, Garrett & Dunner, LLP (57) ABSTRACT

Disclosed are a method and an apparatus (2) for analyzing a body fluid sample from a sampler, the apparatus (2) comprising: a sampler bed (4) comprising a plurality of slots (10), each slot being configured to receive a sampler containing a body fluid sample; an analyzing unit configured to analyze body fluid samples; at least one inlet (6) configured to withdraw a body fluid sample from a sampler from any of
(Continued)

the slots (10) for provision of the withdrawn body fluid sample to the analyzing unit; and at least one display unit comprising at least one display area (8); the apparatus being configured to display graphical information simultaneously within a plurality of primary zones (12) of the at least one display area, wherein the plurality of primary zones comprises a primary zone for each slot (10), and wherein each of the primary zones (12) individually faces a respective slot (10), and wherein the graphical information comprises a respective primary graphical information part within each primary zone, and wherein each respective primary graphical information part relates to the respective slot faced by the respective primary zone.

23 Claims, 7 Drawing Sheets

(51) Int. Cl.
    *G01N 35/00*     (2006.01)
    *G16H 10/40*     (2018.01)
    *G01N 35/02*     (2006.01)
    *G01N 35/10*     (2006.01)

(52) U.S. Cl.
    CPC ......... *G01N 35/02* (2013.01); *G01N 35/1009* (2013.01); *G16H 10/40* (2018.01)

(56) References Cited

U.S. PATENT DOCUMENTS

| | | | |
|---|---|---|---|
| 5,880,725 A * | 3/1999 | Southgate | G06F 3/0485 |
| | | | 715/790 |
| 6,689,318 B1 | 2/2004 | Spork et al. | |
| 6,950,993 B2 * | 9/2005 | Breinberg | G06F 8/38 |
| | | | 715/788 |
| 9,256,349 B2 * | 2/2016 | Phillips | G06F 3/04842 |
| 2003/0029254 A1 | 2/2003 | Hvidtfeldt et al. | |
| 2003/0126914 A1 | 7/2003 | Hvidtfeldt et al. | |
| 2005/0229110 A1 | 10/2005 | Gegner et al. | |
| 2016/0011120 A1 | 1/2016 | Ringemann et al. | |
| 2016/0054307 A1 | 2/2016 | Pinkowitz et al. | |

FOREIGN PATENT DOCUMENTS

| | | |
|---|---|---|
| CN | 104854457 A | 8/2015 |
| CN | 204740254 U | 11/2015 |
| EP | 2 335 569 A2 | 6/2011 |
| JP | 5-72215 | 3/1993 |
| JP | 10-512677 | 12/1998 |
| JP | 2006-510883 | 3/2006 |
| JP | 2016-211948 | 12/2016 |
| WO | WO 2015/153254 A1 | 10/2015 |

OTHER PUBLICATIONS

Written Opinion of the International Searching Authority for International Application No. PCT/EP2017/081316 (five pages).

* cited by examiner

APPARATUS AND A METHOD FOR ANALYZING A BODY FLUID SAMPLE FROM A SAMPLER

This application is a national stage filing under 35 U.S.C. § 371 of International Application No. PCT/EP2017/081316, filed on Dec. 4, 2017, which claims priority of Danish Patent Application No. PA 2016 00791, filed on Dec. 23, 2016. The contents of these applications are each incorporated herein by reference.

TECHNICAL FIELD

The present disclosure relates to an apparatus and a method for analyzing a body fluid sample from a sampler.

BACKGROUND

An emergency department (ED), also known as an accident & emergency department, emergency room or casualty department, is a medical treatment facility specializing in emergency medicine, in particular acute care of patients who normally arrive without prior appointment. Furthermore, patients may be unconscious, and information such as their medical history, allergies, and blood type may be unavailable at the time of arrival. Due to the unplanned nature of patient attendance at an ED, the ED must be able to provide initial treatment for a broad spectrum of illnesses and injuries, some of which may be life-threatening and require immediate attention. Accordingly, fast decisions—in particular on life-or-death cases—are critical at an ED.

As a result, doctors at an ED often face great pressures to test for various and numerous aspects relating to the patient. A plurality of such aspects may be deduced from a single body fluid sample, such as a blood sample, from one patient by means of an analyzing unit for analyzing body fluid. Furthermore, results from analyzing a body fluid sample may be provided relative fast, such as within one or a few minutes, e.g. by a blood analyzing unit. In consequence, there is often an encouragement for extracting a body fluid sample from all or most patients at an ED and to analyze these samples at the ED. Sampling is usually understood as gathering of matter, such as body fluid, from the body of a patient in order to aid in the process of a medical diagnosis and/or evaluation of an indication for treatment, further medical tests or other procedures. In this sense, a sample is the gathered matter (such as a body fluid sample from a patient), and a sampling tool (also known as a sampler) is a device used to acquire and/or contain a sample from the sampled body. Because time is such an essential factor in emergency treatment, the EDs typically have their own diagnostic equipment, which equipment is used by the ED staff. This is to avoid waiting for equipment and staff elsewhere, such as in the same hospital, where specialists in handling samplers otherwise may be located. Furthermore, an ED may operate 24 hours a day, which puts additional stress one the ED staff working at hours of the day where they otherwise would be at sleep. Furthermore, a plurality of patients—and samplers—are often handled in parallel, and these patients and/or samplers are often handled by a plurality of ED staffs.

Automated handling of samplers is known from the "ABL800 FLEX blood gas analyzer", which enables handling of up till three samplers at any time. Each sampler may sequentially have the contained sample withdrawn and subject to analysis followed by display of information relating to the results of the analysis.

Therefore, there is a need in the industry to overcome the abovementioned and other shortcomings.

SUMMARY

The inventors of the present invention have realized a need for providing a method and an apparatus for analyzing a body fluid sample from a sampler, which method and apparatus offers improved usability and decreased cause of fatigue due to use thereof—in particular when used by a plurality of personnel and/or when handling a plurality of samplers, such as but not limited for use at an ED.

The present invention may not be limited for use at an ED. The method and the apparatus of the present invention may be used at any location. Non-limiting examples hereof include: any kind of hospitals and laboratories, where analysis of a body fluid sample, such as a blood sample, from a sampler is to be carried out.

According to a first aspect of the present invention there is provided an apparatus for analyzing a body fluid sample from a sampler. The apparatus comprises: a sampler bed, an analyzing unit, at least one inlet, and at least one display unit. The sampler bed comprises a plurality of slots, each slot being configured to receive a sampler containing a body fluid sample. The analyzing unit is configured to analyze body fluid samples. The at least one inlet is configured to withdraw a body fluid sample from a sampler from any of the slots for provision of the withdrawn body fluid sample to the analyzing unit. The at least one display unit comprises at least one display area. The apparatus is configured to display graphical information simultaneously within a plurality of primary zones of the at least one display area. The plurality of primary zones comprises a primary zone for each slot. Each of the primary zones individually faces a respective slot. The graphical information comprises a respective primary graphical information part within each primary zone. Each respective primary graphical information part relates to the respective slot faced by the respective primary zone.

According to a further aspect of the present invention there is provided a method for analyzing a body fluid sample from a sampler. The method comprises receiving a sampler containing a body fluid sample at a slot of a sampler bed comprising a plurality of slots. The method comprises withdrawing the body fluid sample from the sampler. The method comprises providing the withdrawn body fluid sample to an analyzing unit configured to analyze body fluid samples. The method comprises displaying graphical information simultaneously within a plurality of primary zones of at least one display area. The plurality of primary zones comprises a primary zone for each slot. Each of the primary zones individually faces a respective slot. The graphical information comprises a respective primary graphical information part within each primary zone. Each respective primary graphical information part relates to the respective slot faced by the respective primary zone. The above listing of steps of a method for analyzing a body fluid sample from a sampler may be carried out in any other order than the above-mentioned. For instance, "displaying graphical information" may be provided prior to "receiving a sampler".

Accordingly, there is provided an apparatus and a method inflicting reduced stress on the eyes of the user compared to known solutions. Reduced stress is provided since the eyes of the user have to move less in order to identify and/or verify a relation/correspondence between a respective slot and related information on the at least one display area.

Furthermore, and/or in consequence hereof, there is a lower risk for the user to mix up samplers and/or corresponding test results.

The present disclosure relates to different aspects including the apparatus described above and in the following and to corresponding methods, such as described above and in the following. Each aspect may yield one or more of the benefits and advantages described in connection with one or more of the other aspects, and each aspect may have one or more embodiments with all or just some of the features corresponding to the embodiments described in connection with one or more of the other aspects and/or disclosed in the appended claims.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings, where like reference numerals will be used for like elements.

The accompanying drawings are included to provide a further understanding of the invention, and are incorporated in and constitute a part of this specification. The drawings illustrate embodiments of the invention and, together with the description, serve to explain the principals of the invention.

Other and further aspects and features will be evident from reading the following detailed description of the embodiments.

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DETAILED DESCRIPTION

The apparatus according to the present invention may be configured for analyzing a body fluid sample comprising or consisting of any of the following: {human blood, pleural fluid, dialysis fluid, or urine}.

The apparatus may comprise elements from any known apparatus, such as any known blood gas analyzer, and/or may function in a similar manner.

The sampler bed may comprise a frame supporting the slots. The slots may be individually, movably attached to the frame. Movement of an individual slot may be utilized in connection with withdrawal of the body fluid sample from a respective sampler from a respective slot, whereby a connection from the respective sampler to the at least one inlet may be established. The slots of the apparatus may be understood as a plurality of slots. The plurality of slots may comprise or consist of the following number of slots: {2, 3, 4, or more}.

The sampler bed may be movable in relation to the first inlet. Movement of the sampler bed may be utilized in connection with withdrawal of the body fluid sample from a respective sampler from a respective slot, whereby a connection from the respective sampler to the at least one inlet may be established Alternatively, or in combination, the first inlet (or a plurality of inlets) may be movable in relation to the sampler bed and/or the respective individual slot.

Alternatively, or in combination, a respective sampler may be connected to the at least one inlet without movement of any of {the sampler bed, the respective slot, or the inlet} in relation to another.

A slot may comprise or be defined by a recess in the sampler bed, which recess is configured to receive and/or hold a sampler. A slot may be understood as a port or a receptacle or any part being configured to receive and/or hold a sampler. A slot may have an extension in one direction being longer than in another direction, but may not be limited to such.

When referring to a position, or placement of a slot this may be understood as the position, or placement of a sampler being held and/or received by the respective slot.

A slot may be configured for receiving a sampler having an elongate form.

Receiving a sampler containing a body fluid sample may be effectuated by manually placing such sampler on/at/in the respective slot.

The analyzing unit, which is configured to analyze body fluid samples, may be provided as known in the field of analyzing units. The analyzing unit may for instance be configured to analyze blood gas.

The at least one inlet may comprise an aperture, configured for coupling with the sampler for withdrawal of the content (i.e. the sample) of the sampler.

"Withdraw" may also be known as "aspirate". When a body fluid sample is withdrawn from a sampler, the entire (or substantially entire) content of the respective sampler may be withdrawn. However, residues may remain in the respective sampler. Alternatively, only part of the sample may be withdrawn. When a nurse takes a blood sample from a patient, she fills the sampler at least until a minimum fill line. The minimum fill line ensures that the volume of blood is sufficient for diluting the chemistry within the sampler into the blood without interfering with the constituents of the blood. However, the analyzer aspirates a fixed volume from the sampler which is less than the volume within the sampler when filled to the minimum fill line.

A withdrawn sample may be provided to the analyzing unit immediately after being withdrawn from the respective sampler. The apparatus of the present invention may comprise a tubing system for provision of a withdrawn sample from the inlet to the analyzing unit. Such tubing system may be considered as forming part of the inlet and/or analyzing unit.

The at least one display unit comprising at least one display area may be provided by means of any display device, such as any electronic display. Non-limiting examples includes: {Light-emitting diode display (LED), Electroluminescent display (ELD), Electronic paper, E Ink, Plasma display panel (PDP), Liquid crystal display (LCD), High-Performance Addressing display (HPA), Thin-film transistor display (TFT), Organic light-emitting diode display (OLED)}. The at least one display unit may comprise a first display unit. The at least one display area may comprise a first display area. The first display unit may comprise the first display area.

The at least one display area may be flat, such as being substantially flat. The at least one display area may comprise one or more curved parts, such as one or more curved edges.

Display of graphical information simultaneously within a plurality of primary zones, may be understood as a perceived simultaneous or concurrent presence as perceived by a user of the apparatus.

Each of the plurality of primary zones may be defined within the at least one display area.

The number of primary zones may be equal to the number of slots.

The plurality of primary zones may face the plurality of slots.

A respective primary graphical information part may be understood as all graphical information within a respective primary zone.

Each respective primary graphical information part may relate to the respective slot faced by the respective primary zone. "Relate to" may be understood as "refer to" and/or "comprising information of".

The plurality of primary zones may be defined within the first display area. The first display area may define a first edge. The first display area may define four edges. The first edge may be defined as the edge of the first display area being closest to the sampler bed taken from the plurality of edges, such as four edges.

The plurality of primary zones may be provided such that the first edge of the first display area is closer to the plurality of slots than the plurality of primary zones is to the slots.

The plurality of primary zones may border the first edge.

The plurality of primary zones may be provided such that the first edge of the first display area is located between the plurality of primary zones and the plurality of slots. In this connection (and throughout the present disclosure, where one part is defined as being between two other parts), "between" may be understood as seen from the point of view of the user and/or the intended point of view of the user. The intended point of view of the user may be defined as an area or point in space in front of the sampler bed and the at least one display area. This may be within 20 cm to 110 cm of the sampler bed and within 20 cm to 110 cm of the at least one display area, and/or within "an arm's reach" of both. This is further illustrated by means of FIG. 6 below.

The at least one display area (such as the first display area) and the sampler bed may be inclined in relation to each other. The inclination may be defined between a first plane, defined by the at least one display area, and a second plane, defined by the sampler bed. A second plane defined by the sampler bed may for instance be understood as a general elongate direction formed by the plurality of slots, if such form is provided by the slots. Alternatively, or in combination, such second plane may be defined by a general elongate direction formed by a plurality of samplers held by the sampler bed.

Each of the primary zones may individually face the respective slot such that: each slot defines a respective proximity point on a first edge of the at least one display area (such as a first edge of a first display area), wherein each respective proximity point being defined as the point on the first edge being closest to the respective slot, and wherein each primary zone is closer to the proximity point defined by the related slot than to any other proximity point defined by another slot.

Each of the primary zones may individually face the respective slot such that: each primary zone defines a respective proximity point on a first edge of the at least one display area (such as a first edge of a first display area), wherein each respective proximity point being defined as the point on the first edge being closest to the respective primary zone, and wherein each slot is closer to the proximity point defined by the related primary zone than to any other proximity point defined by another primary zone.

The proximity points defined by a primary zone and the related slot, respectively, may coincide.

NB: it is understood that "the primary zones individually facing a respective slot" occurs at least temporarily during use of the apparatus, such as for a first position of the sampler bed during use of the apparatus. Accordingly, the primary zones may not always face the related slots. For instance, the sampler bed may temporarily be displaceable in relation to the at least one display area, such as in relation to the first display area.

The term "face" may be understood such that each of the respective individual primary zones being closer to the related slot than to any other slot.

The term "slot" may be understood as a place/part on or of the apparatus, such as a spot thereon/thereof. A slot does not necessarily have an elongate shape. The shape of individual slots may be adapted to the shape of the samplers.

The graphical information (such as the primary graphical information part displayed at one, more, or all primary zones, and/or the secondary graphical information as defined below) may comprise one or more letters or symbols, such as one or more words, digits, or numbers. For instance, the primary graphical information part may indicate, e.g. using one or more words, whether a sampler: {can be placed at; should be removed from; should not be removed from; cannot be placed at, or should not have been removed from} the related slot. The latter case may for instance cover a situation where a user has removed a sampler that should not have been removed from the slot. Accordingly, the user may be prompted to "Replace sampler" (i.e. place the respective sampler at the respective slot once again or at another vacant slot).

The at least one inlet may comprise a common inlet and/or an inlet for each slot. A common inlet may be configured to be manually used for withdrawing a sample from a sampler without use of the sampler bed and/or a respective slot.

The at least one display area may comprise one or more touch-sensitive areas enabling the user to interact. Other means of interaction may be provided, e.g. by provision of control by means of a keyboard and/or a curser control.

Interaction may for instance comprise selecting a sampler and/or slot and/or sample by clicking or touching the related primary zone.

Information relating to a respective slot may comprise information relating to any one or more of the following: {the availability state of the respective slot (e.g. whether or not a sampler can be placed, should be removed, or should not be removed); the sample or sample content which is or was contained by the sampler that is or was received/held by the respective slot; the operator (e.g. the one obtaining the before-mentioned sample from a patient); the before-mentioned patient; etc.}.

The primary information may relate to any one or more of: {the sampler and the slot} while the secondary information (as defined below) may relate to any one or more of: {the sample, the patient, and the operator}.

A sampler may comprise or form part of a syringe and/or a capillary tube. The apparatus according to the present invention may be configured to be used with a sampler comprising a built-in mixing ball, such as a magnetically manipulable sphere that may be actuated by means of a changing magnetic field. Such magnetic field may be generated by the apparatus of the present invention by means of a suitable unit thereof. Accordingly, the content of a sampler may be mixed while the sampler is placed at a slot. This may impede a sample of e.g. blood from coagulating while waiting for the sample to be withdrawn and provided to the analyzing unit.

Each slot may define a respective proximity point on a first edge of the at least one display area, such as a first edge of a first display area. Each respective proximity point may be defined as the point on the first edge being closest to the respective slot, i.e. compared to any other points on the first edge. The term "closest to" may be understood as the one point of the first edge being in average closest to each point/part of the respective slot.

Each primary zone may be closer to the proximity point defined by the related slot than to any other proximity point defined by another slot.

Accordingly, when a user needs to visually locate the primary zone relating to a specific slot, a reduced level of stress may be provided to the eyes of the user since the eyes have to move the least by first looking perpendicular into the edge of the (first/at least one) display area and then moving to the nearest primary zone, which may even border the edge.

A proximity point may be defined vice versa with respect to primary zone and the related slot. Accordingly, similar advantage may be provided when a user needs to visually locate the slot relating to a specific primary zone.

A slot relating to a primary zone may be understood as the slot being related to by the primary zone.

The plurality of slots may form a first alignment. The respective primary zones may form a second alignment. The second alignment may be parallel to the first alignment. Accordingly, the eyes of the user may move in a similar manner for each "pair" of slot/primary zone in order to confirm a correspondence/relationship between each a respective slot and the related primary zone. The term "related primary zone" may be understood as the primary zone relating to the respective slot.

The plurality of slots and the respective primary zones may be arranged in a grid-like structure. A grid-like structure may be understood as a network comprising uniformly spaced horizontal lines and/or uniformly spaced perpendicular lines. Other grid structures may be provided. Accordingly, intersecting lines may define the positions of the primary zones/slots.

Each primary zone may form a primary alignment with the related slot, such that all primary alignments are parallel. This may alleviate use of the eyes of the user.

The distance between a primary zone and the related slot may be less than 20 cm, such as less than: 15 cm, 10 cm, or 5 cm. The distance between a first edge of the at least one display area and the plurality of slots may be less than 20 cm, such as less than: 15 cm, 10 cm, or 5 cm. The distances as defined above may be defined as being between the closest parts thereof.

Throughout the present disclosure, the distance between two parts/elements may be understood as the distance between the closest points of the respective parts/elements.

The distance between two primary zones may correspond to the distance between the two slots relating to the respective primary zones.

The plurality of slots may comprise three slots. For any embodiment comprising three slots, i.e. at least three slots, the distances between adjacent primary zones may be the same.

The at least one primary graphical information part may comprise color-coded information. This may for instance include "binary" color-coding (i.e. use of color coding by means of two different colors), e.g. using green/orange, or any other combination of two different colors, to indicate availability/no availability of a slot. For instance, each primary zone relating to a slot being vacant may comprise a first color, e.g. green, and each primary zone relating to a slot not being vacant may comprise a second color, e.g. red/orange.

Information may be coded by means of light intensity instead of or in combination with color-coded information. For instance, in case any action may be required by the user, such as removal of a sampler from a slot, the light intensity of at least a part of the related primary zone may be changed accordingly.

The at least one primary graphical information part may comprise information relating to a status of the related slot, such as: {vacant, "occupied—busy", "error—to be removed", "aspirated (finished)—to be removed", etc.}.

The at least one primary graphical information part may comprise information relating to a sampler held by the related slot, such as information relating to a status of the sampler, such as: "under processing", or such as: information identifying the sampler.

The apparatus according to the present invention may comprise a plurality of intermediate display parts, which may comprise an intermediate display part for each slot. Each intermediate display part may be provided between a respective slot and the at least one display area. The term "between" may be understood as defined above, i.e. e.g. with respect to the (intended) point of view of the user. Accordingly, the respective intermediate display parts may guide the eyes of the between a primary zone and the related slot.

Each intermediate display part may be configured to display respective intermediate information relating to the respective slot.

Each intermediate display part may be provided such that the distance between the respective intermediate display part and the at least one display area is smaller than the distance between the related slot and the at least one display area.

Each intermediate display part may be provided such that the distance between the respective intermediate display part and a first edge of the at least one display area (such as a first edge of a first display area) is smaller than the distance between the related slot and the first edge of the at least one display area.

The distance between a respective intermediate display part and the related slot may be less than 10 cm, such as less than 5 cm.

Each intermediate display part may be provided between the respective slot and the primary zone relating to the respective slot. The term "between" may be understood as defined above, i.e. e.g. with respect to the (intended) point of view of the user. Accordingly, the respective intermediate display parts may guide the eyes of the user between a primary zone and the related slot.

The apparatus may be configured to indicate a status for a related slot by means of the respective intermediate display part.

Each intermediate display part may comprise a light emitting part, such as an LED.

The intermediate display parts may be integrated with and/or supported by the sampler bed, such as by a frame of the sampler bed.

The primary graphical information part displayed at a primary zone and/or the intermediate information displayed by an intermediate display part may comprise pulsating and/or varying intensity visuals, such as a fixed or variable frequency rhythm. For variable frequency pulsation visuals, information may for instance be coded by means of the frequency. For instance by indicating whether action is required, or not. For instance, a relatively slow blink may indicate that attention/input/action from user is required. For instance, a relatively fast blink may indicate an error. This may indicate that the related sampler held by the related slot must be removed.

Accordingly, information may be understood as the mere presence of visuals, which can be interpreted by a user.

LEDs may be controlled using an on/off-scheme, whereby each LED is either on or off. A switching being faster than e.g. 50 Hz may be utilized for creating an illusion of dampening the respective LED.

Pulsating visuals at an intermediate display part may be in particular an advantage since attention may be drawn fast and reliable to a particular sampler/slot as well as to related information, such as presented at the primary zone and/or elsewhere on the at least one display unit/at least one display area. A relative slow blink may indicate a need to input information, such as using a touch sensitive area of the secondary zone (as defined below).

The apparatus according to the present invention may be configured to display secondary graphical information at a secondary zone of the at least one display area. The secondary graphical information may relate to a slot of a selected primary zone, i.e. a slot relating to the selected primary zone. The secondary zone may be provided such that the related primary zone is provided between the selected slot and the secondary zone.

The term "between" may be understood as defined above, i.e. e.g. with respect to the (intended) point of view of the user. Accordingly, the selected primary zones may guide the eyes of the user between the secondary zone and the related slot of the selected primary zone.

The secondary zone may be provided such that the distance between the selected primary zone and the related slot is smaller than the distance between the secondary zone and the related slot.

The secondary zone may be provided such that the selected primary zone is between the secondary zone and the proximity point defined by the related slot.

The secondary zone may be provided such that the selected primary zone is between the secondary zone and the first edge of the first display area.

The term "selected" may be understood as: selected by a user and/or the apparatus. A user selection may for instance be by actively clicking or touching the respective primary zone. A selection by the apparatus may be in response to various aspects, such as any one or more of the following:

{response to user interaction with a sampler (such as placing or removing); in response to a result obtained from the analyzing unit; in response to an alert e.g. if anything happens that needs attention by the user}.

The apparatus may be configured to display which primary zone is selected. This may for instance be by any of the methods as described in the present disclosure, such as by means of any one or more of the following: {pulsating and/or varying intensity visuals; color-coded information; change in size of displayed information of the selected primary zone (such as a larger size) and/or a change of the size of the zone itself (such as enlarging the selected zone compared to the non-selected zone and/or prior to being selected)}. The apparatus may be provided such that only one zone may be selected at a time.

The secondary zone may be adjacent to each of the primary zones. The secondary zone may border each of the primary zones. Each of the primary zones may border and edge (such as the first edge) of the at least one display area (such as the first display area).

The secondary graphical information may for instance be information relating to a sample retrieved from the sampler from the respective slot.

The secondary graphical information may remain on the at least one display unit/at least one display area even if this information becomes obsolete with respect to the content and/or information of the slot relating to the selected primary zone. The secondary graphical information may for instance remain on the at least one display unit/at least one display area until a user makes appropriate action or until a preset time has elapsed, e.g. whichever occurs first. Once a primary zone is selected the related secondary information may for instance remain on the secondary zone until a specific event occurs. Such event may comprise one or more of the following: {the user un-select the presented information; another primary zone is selected (e.g. by the user placing a sampler at a slot relating to another primary zone); the apparatus and/or the at least one display unit enters an idle state, which for instance can be after a preset time has elapsed since the last interaction or selection or another change in information. This preset time may for instance be anything from 20 seconds to 3 hours or more. Any value between is possible, such as 2 minutes or 5 minutes.}

For instance, a sampler may be removed from a slot, which may change the primary graphical information part. This may then not affect any related info displayed on the secondary zone—e.g. until an appropriate action is taken by the user.

The secondary graphical information may supplement the related primary graphical information part. In this connection, the term "supplement" may be understood as: providing information in addition to what is provided by means of the respective primary graphical information part.

The secondary graphical information may for instance appear after a sampler is provided at a slot. Accordingly the user may be requested to enter information relating to the sampler.

After a sampler is provided at a slot manual and/or automatic identification of the sampler may be carried out.

The apparatus may comprise an identifier unit configured to identify a sampler automatically. This may for instance be carried out by means of a barcode on the respective sampler and a barcode scanner provided at or with the apparatus.

The secondary graphical information may for instance appear when input relating to a sampler needs to be provided.

The secondary graphical information may for instance appear when a result from the analyzing unit relating to a sampler is ready.

The secondary graphical information may for instance appear when urgent attention from the user is needed—e.g. if an error is observed.

The secondary graphical information may for instance appear if the apparatus is in a "busy" state, e.g. once a sample from a sampler is being withdrawn.

The at least one inlet may comprise a first inlet configured to withdraw the body fluid sample from a sampler from any of the slots.

The user may need to enter (further) information, e.g. via the one or more touch-sensitive areas of the at least one display unit/at least one display area, such as within the secondary zone.

Figure 1:
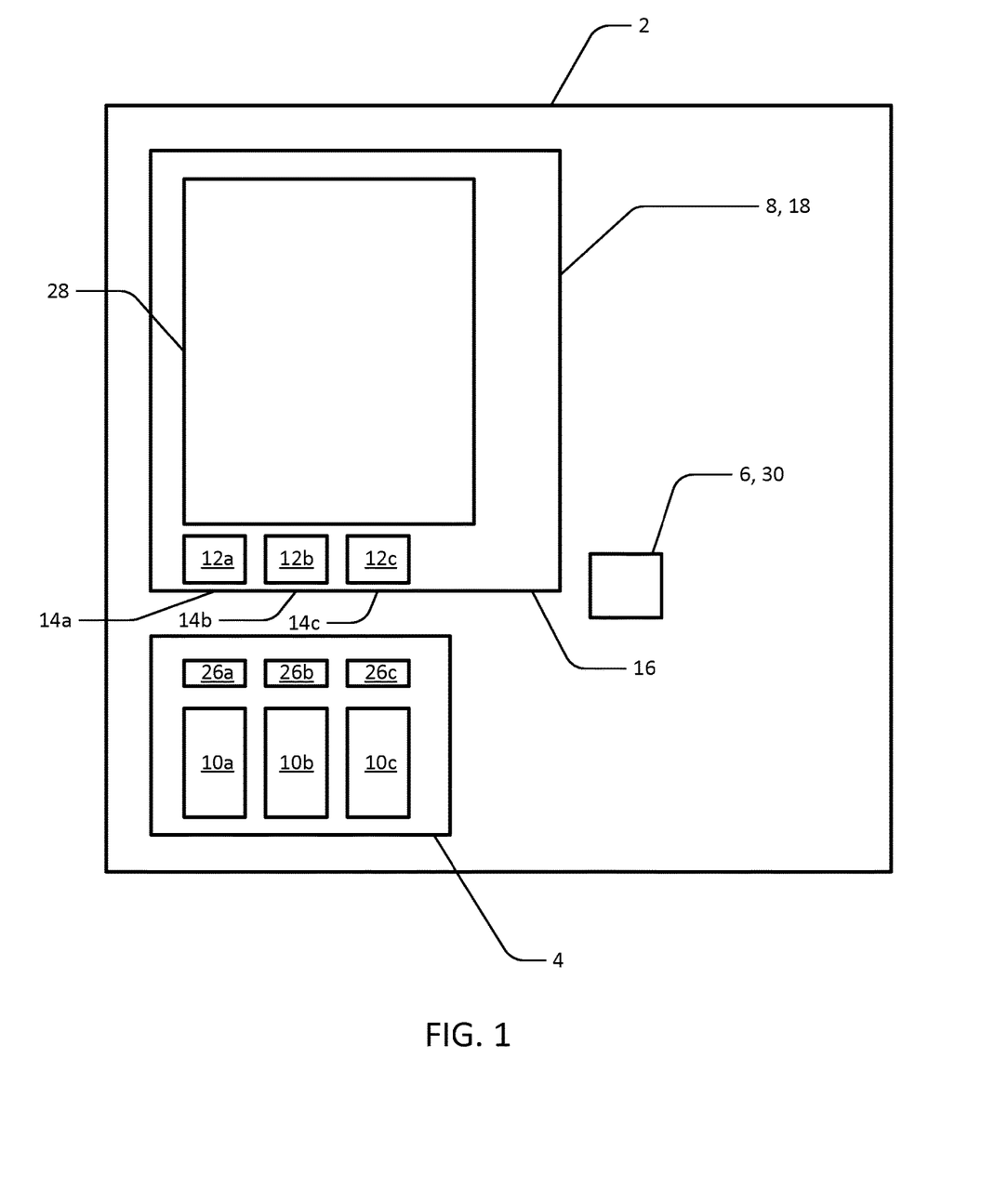
FIG. 1 schematically illustrates a first embodiment of an apparatus according to the present invention.

The apparatus may comprise one or more sensors configured to detect receipt of a sampler at a slot. Use of the apparatus and/or the method according to the present invention may comprise one or more of the following steps in the following order or in another order:

User reads one or more primary graphical information parts
User locates a vacant slot
User places sampler at the previously vacant slot
A sensor detects the sampler at the slot
The corresponding intermediate display part shows updated intermediate information related to the slot
Display unit shows updated status/information relating to the slot in the related primary zone
identifier unit identifies the received sampler automatically
Display unit shows updated status/information about the received sampler within the related primary zone
User enters additional information in Secondary zone
User approves the displayed information in Secondary zone by pressing a button in the Secondary zone
Queue mixer starts to mix sampler content
Sampler bed moves Sampler slot to Inlet
the inlet aspirates sample from sampler
Sampler bed moves back to position below display
User waits for analysis of sample from the analyzing unit to be finished
User reads results from Secondary zone FIG. 1 schematically illustrates a first embodiment of an apparatus 2 according to the present invention for analyzing a body fluid sample from a sampler (not illustrated). The apparatus 2 comprises: {a sampler bed 4; an analyzing unit (cf. ref. 92 in FIG. 7); at least one inlet 6; and at least one display unit comprising at least one display area 8}. The at least one display area comprises a first display area 18. The sampler bed 4 comprises a plurality of slots 10 (three slots: 10a, 10b, and 10c), each slot 10 being configured to receive a sampler containing a body fluid sample. The analyzing unit is configured to analyze body fluid samples. The least one inlet 6 is configured to withdraw a body fluid sample from a sampler from any of the slots 10 for provision of the withdrawn body fluid sample to the analyzing unit. In FIG. 1, the sampler bed 4 is in a first position. Throughout the present disclosure, the ref. 10 refers to any or all of: {10a, 10b, 10c}. The same applies for the below-mentioned refs. 12, 14, 24, 26, 40, and 42, mutatis mutandis.

The apparatus 2 is configured to display graphical information simultaneously within a plurality of primary zones 12 (three primary zones: 12a, 12b, and 12c) of the at least one display area 8. The plurality of primary zones comprises a primary zone 12a, 12b, 12c for each slot 10a, 10b, 10c.

Each of the primary zones 12 individually faces a respective slot 10. For instance; the primary zone 12a faces the slot 10a; the primary zone 12b faces the slot 10b; and the primary zone 12c faces the slot 10c. The graphical information comprises a respective primary graphical information part within each primary zone 12a, 12b, 12c. Each respective primary graphical information part relates to the respective slot 10 faced by the respective primary zone 12. For instance, the primary graphical information part within the primary zone 12a relates to the respective slot 10a faced by the respective primary zone 12a.

Each slot 10a, 10b, 10c defines a respective proximity point 14a, 14b, 14c on a first edge 16 of the first display area 18. Each respective proximity point 14a, 14b, 14c is defined as the point on the first edge 6 being closest to the respective slot 10a, 10b, 10c. Each primary zone 12 is closer to the proximity point 14 defined by the related slot 10 than to any other proximity point 14 defined by another slot 10. For instance, the primary zone 12b is closer to the proximity point 14b defined by the related slot 10b than to any other proximity point 14a, 14c defined by another slot 10a, 10c, respectively.

Figure 2:
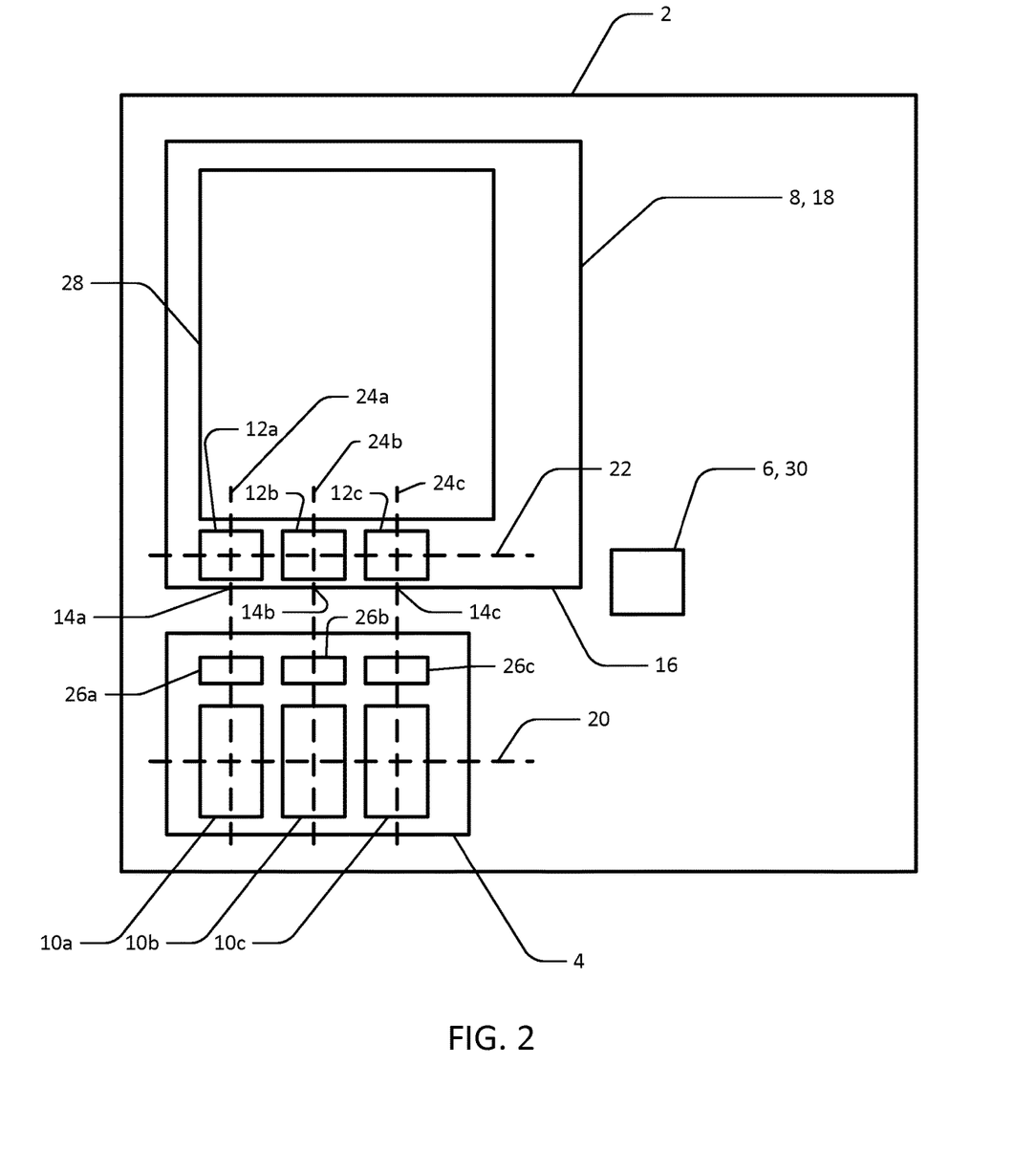
FIG. 2 schematically illustrates the embodiment of FIG. 1 with superimposed dotted lines illustrating alignments of parts of the apparatus.

FIG. 2 schematically illustrates the embodiment of FIG. 1 with superimposed dotted lines 20, 22, 24a, 24b, 24c illustrating specific alignments of parts of the apparatus. The plurality of slots 10 forms a first alignment (illustrated by means of the extended dotted line 20 in FIG. 2). The primary zones 12 form a second alignment (illustrated by means of the extended dotted line 22 in FIG. 2). The second alignment 22 is parallel to the first alignment 20.

The plurality of slots 10 and the respective primary zones 12 are arranged in a grid-like structure.

Each primary zone 12 forms a primary alignment 24 (three primary alignments: 24a, 24b, and 24c, illustrated by means of the respective extended dotted lines 24a, 24b, 24c in FIG. 2) with the related slot 10. All primary alignments 24 are parallel. For instance, the primary zone 12a forms a primary alignment 24a with the related slot 10a.

The distance between a primary zone 12 and the related slot 10 is less than 20 cm.

The distance between two primary zones 12 corresponds to the distance between the related two slots 10. For instance, the distance between the two primary zones 12a and 12b corresponds to the distance between the related two slots 10a and 10b.

For the embodiment illustrated in FIG. 1 the plurality of slots 10 comprises, and consists of, three slots 10a, 10b, 10c. The distances between a primary zone 12b and each adjacent primary zone 12a, 12c are the same. For instance, the distance between 12b and 12a is the same as between 12b and 12c.

The apparatus 2 comprises a plurality of intermediate display parts 26 (three intermediate display parts: 26a, 26b, 26c) comprising an intermediate display part for each slot 10. Each intermediate display part 26 is provided between the respective slot 10 and the at least one display area 8. For instance, the intermediate display part 26a is provided between the respective slot 10a and the at least one display area 8. Each intermediate display part 26 is configured to display respective intermediate information relating to the respective slot 10.

The apparatus 2 is configured to display secondary graphical information at a secondary zone 28 of the at least one display area 8. The secondary graphical information relates to the slot 10 relating to a selected primary zone 12. For instance, if the primary zone 12a is selected, the secondary graphical information will relate to the slot 10a relating to the selected primary zone 12a. The secondary zone 28 is provided such that the related primary zone 12 is provided between the selected slot 10 and the secondary zone 28.

The secondary zone 28 is provided such that each primary zone 12 is between the secondary zone 28 and the respective proximity points 14 defined by the related slots 10.

The secondary zone may border the primary zones. Adjacent primary zones may border each other.

The at least one inlet 6 comprises a first inlet 30 configured to withdraw the body fluid sample from a sampler from any of the slots 10.

Figure 3:
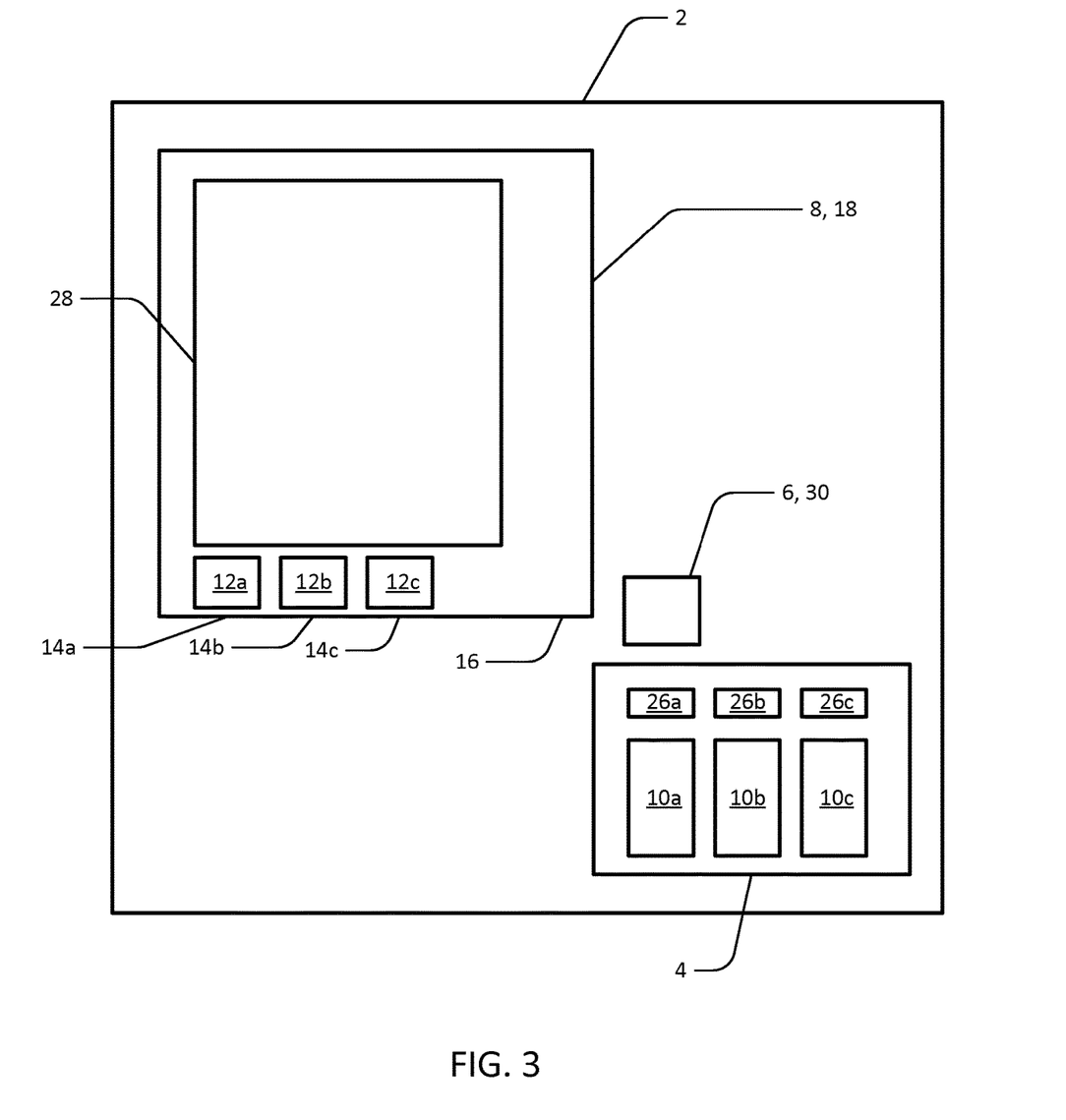
FIG. 3 schematically illustrates the embodiment of FIG. 1, wherein the sampler bed is in a second position.

For the apparatus 2 illustrated in FIGS. 1-3, the sampler bed 4 (including the individual slots 10) is movable in relation to the first inlet 30. This is utilized for withdrawing a respective body fluid sample from a sampler from a slot 10. This is described further in connection with FIG. 3.

FIG. 3 schematically illustrates the embodiment of FIG. 1, wherein the sampler bed 4 is moved to a second position. The second position is utilized for withdrawal of a sample from a sampler (not illustrated) from a slot, such as the slot 10a.

Accordingly, if at least one of: {the sampler bed 4, the at least one display area 8} is moved in relation to the other (such as moving the sampler bed 4 from the first position, as illustrated in FIGS. 1 and 2 to the second position as illustrated in FIG. 3) the primary zones may not individually face the individually related slots.

Figure 4:
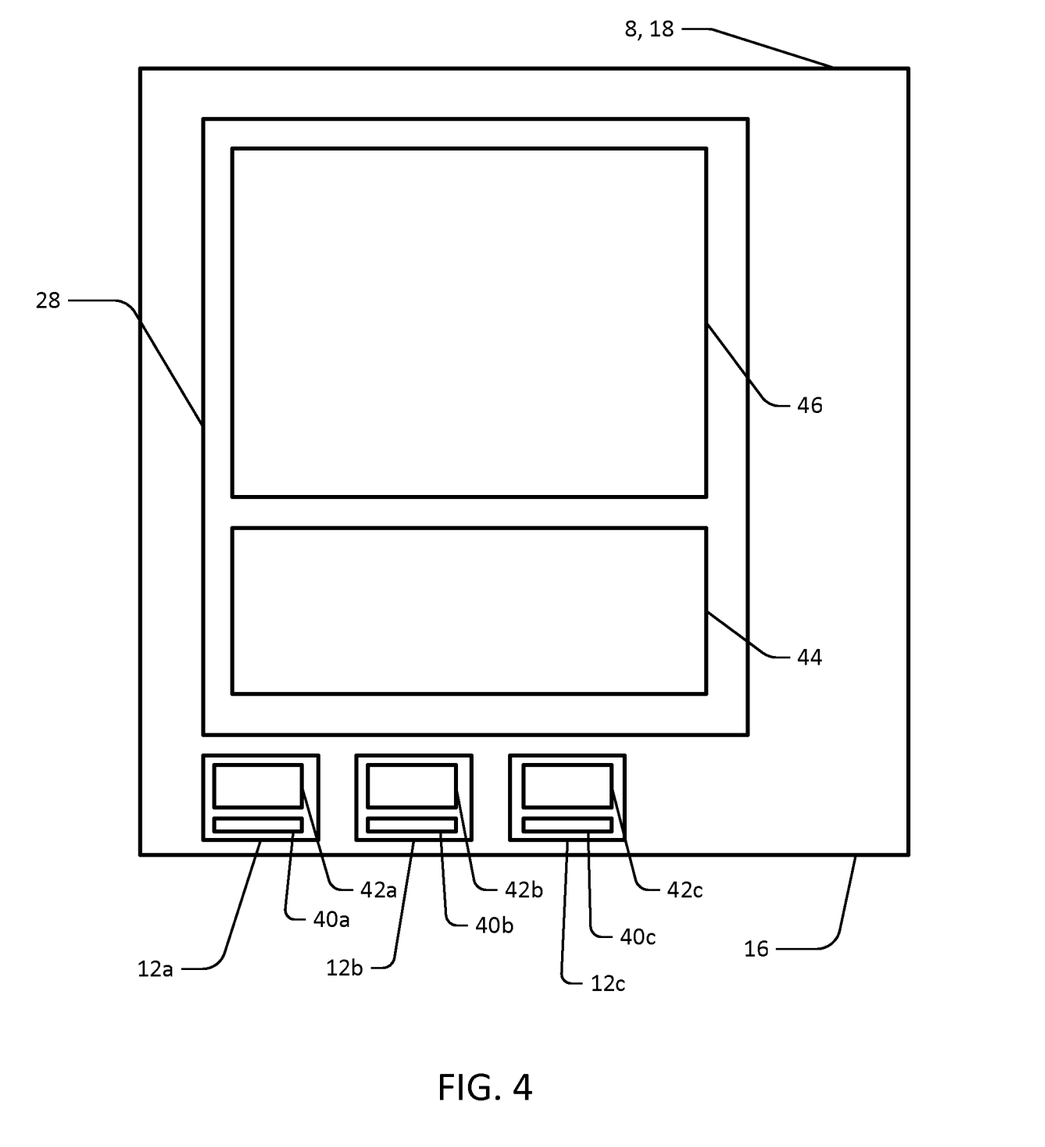
FIG. 4 schematically illustrates exemplary zones of the at least one display area of the apparatus of FIG. 1.

FIG. 4 schematically illustrates exemplary zones of the at least one display area of the present invention. The secondary zone 28 may comprise a plurality of sub-zones 44, 46, e.g. for presenting different secondary information. Each primary zone 12 may comprise a plurality of sub-zones 40, 42, e.g. for presenting different primary information. The sub-zone 40a may for instance provide information being similar to what is provided by the intermediate display part 26, for instance by presenting the same color and/or light intensity and/or varying visual appearance, such as the same frequency of variation of light intensity.

Figure 5:
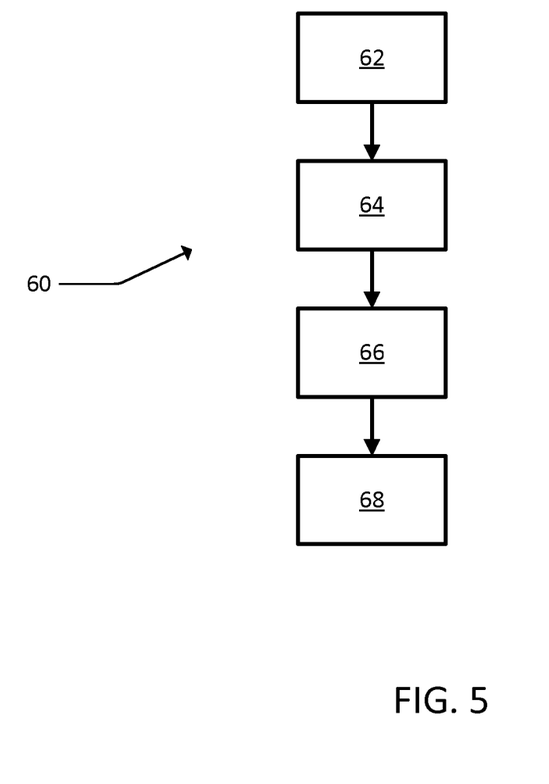
FIG. 5 schematically illustrates a first embodiment of a method according to the present invention.

FIG. 5 schematically illustrates a first embodiment of a method 60 according to the present invention for analyzing a body fluid sample from a sampler. The method 60 comprises receiving 62 a sampler containing a body fluid sample at a slot of a sampler bed comprising a plurality of slots. The method 60 comprises withdrawing 64 the body fluid sample from the sampler using an inlet. The method 60 comprises providing 66 the withdrawn body fluid sample to an analyzing unit configured to analyze body fluid samples. The method 60 comprises displaying 68 graphical information simultaneously within a plurality of primary zones of at least one display area. The plurality of primary zones comprises a primary zone for each slot. Each of the primary zones individually faces a respective slot. The graphical information comprises a respective primary graphical information part within each primary zone. Each respective primary graphical information part relates to the respective slot faced by the respective primary zone.

Figure 6:
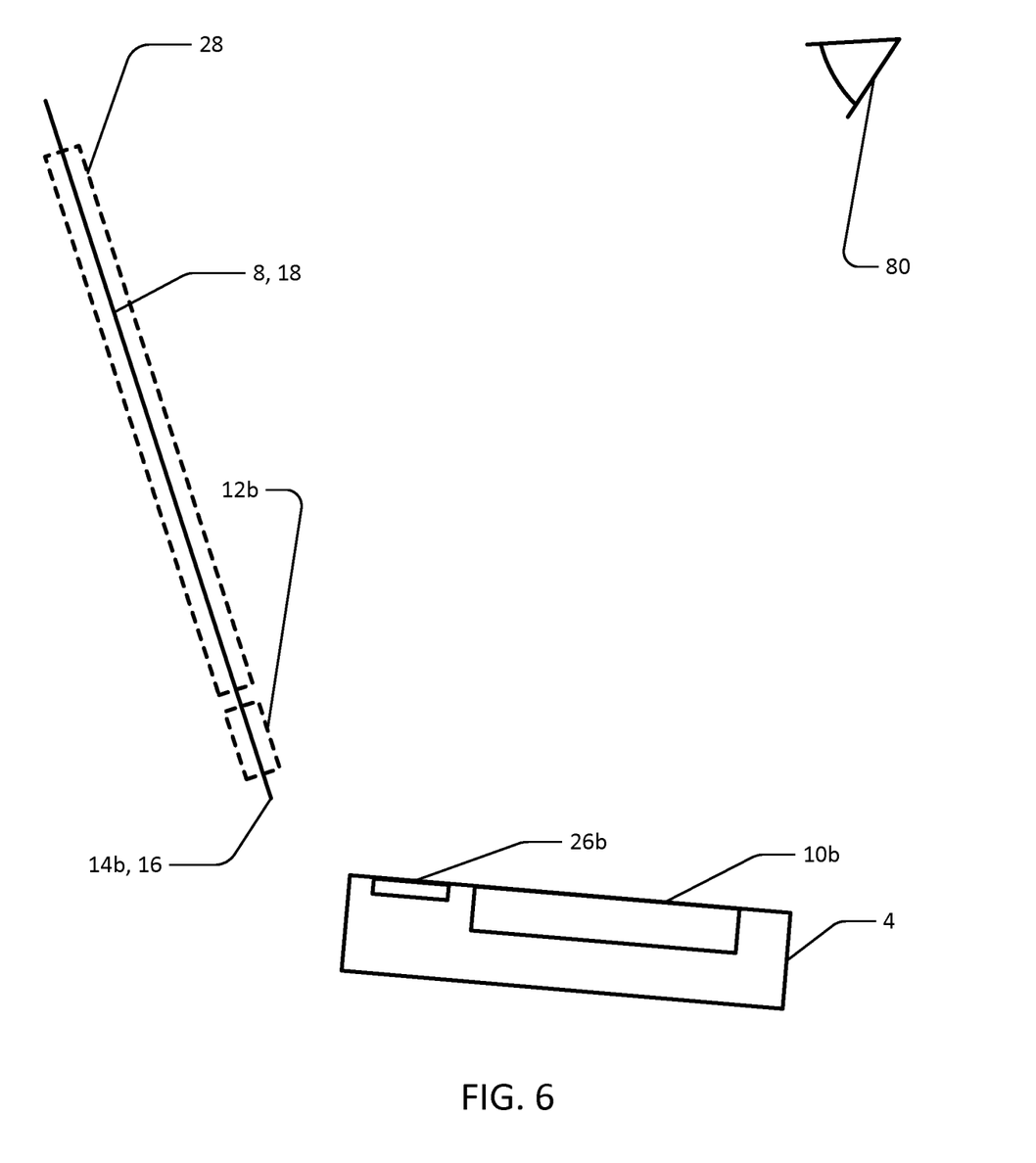
FIG. 6 schematically illustrates a cross-sectional side view of the embodiment of FIG. 1.

FIG. 6 schematically illustrates a cross-sectional side view of the embodiment of FIG. 1 wherein the cross-section is along the dotted line 24b from FIG. 2 in the direction of the dotted line 24c. The primary zone 12b is provided between the secondary zone 28 and the related slot 10b, wherein the term "between" should be understood as with respect to the (intended) point of view 80 of the user (as defined in the present disclosure). Accordingly, the primary zone 12b may guide the eyes of the user between the secondary zone 28 and the related slot 10b of the primary zone 12b.

For illustrative purposes, the primary zone 12b and the secondary zone 28 are marked by means of dotted lines around the respective parts of the at least one display area 8.

The intermediate display part 26b is provided such that the distance between the intermediate display part 26b and the at least one display area 8 is smaller than the distance between the related slot 10b and the at least one display area 8. Furthermore, the distance between the intermediate display part 26b and the related slot 10b is less than 10 cm.

The secondary zone 28 is provided such that the distance between the primary zone 12b and the related slot 10b is smaller than the distance between the secondary zone 28 and the related slot 10b.

Figure 7:
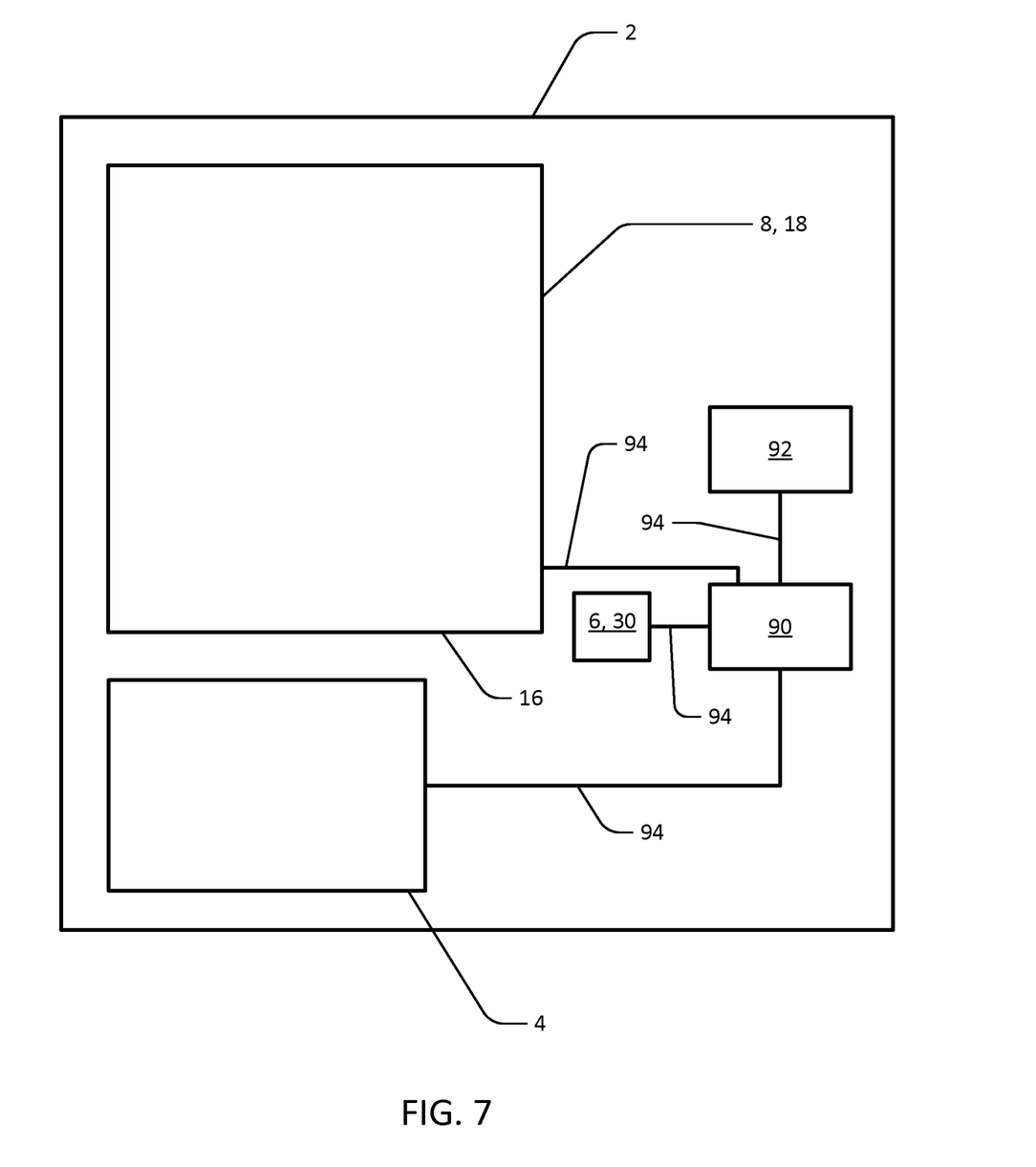
FIG. 7 schematically illustrates a block diagram of the embodiment of FIG. 1.

FIG. 7 schematically illustrates a block diagram of the embodiment of the apparatus 2 illustrated in FIGS. 1-3 and FIG. 6. The apparatus 2 comprises a control unit 90 configured to control: {the sampler bed 4, the at least one inlet 6, the at least one display area 8 of the at least one display unit, and the analyzing unit 92}. This is illustrated by means of respective control lines 94. The control unit 90 may receive results from the analyzing unit 92. The results from the analyzing unit 92 may be provided to the at least one display unit for display on the at least one display area 2.

In apparatus claims enumerating several features, several of these features can be embodied by one and the same item of hardware. The mere fact that certain measures are recited in mutually different dependent claims or described in different embodiments does not indicate that a combination of these measures cannot be used to advantage.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

It should be emphasized that the term "comprises/comprising" when used in the present disclosure is taken to specify the presence of stated features, integers, steps or components but does not preclude the presence or addition of one or more other features, integers, steps, components or groups thereof.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

The invention claimed is:

1. An apparatus for analyzing a body fluid sample from a sampler, the apparatus comprising:
   a sampler bed comprising a plurality of slots, each slot configured to receive a sampler containing a body fluid sample;
   an analyzing unit configured to analyze body fluid samples;
   at least one inlet configured to withdraw a body fluid sample from a sampler from any of the slots for provision of the withdrawn body fluid sample to the analyzing unit; and at least one display unit comprising at least one display area;

wherein the apparatus is configured to display graphical information simultaneously within a plurality of primary zones of the at least one display area, wherein the plurality of primary zones comprises a primary zone for each slot, and wherein each of the primary zones individually faces a respective slot, and wherein the graphical information comprises a respective primary graphical information part within each primary zone, wherein each respective primary graphical information part relates to the respective slot faced by the respective primary zone.

2. An apparatus according to claim 1, wherein each slot defines a respective proximity point on a first edge of the at least one display area, wherein each respective proximity point is defined as the point on the first edge being closest to the respective slot, and wherein each primary zone is closer to the proximity point defined by the related slot than to any other proximity point defined by another slot.

3. An apparatus according to claim 1, wherein the plurality of slots forms a first alignment and the primary zones form a second alignment parallel to the first alignment.

4. An apparatus according to claim 1, wherein the plurality of slots and the primary zones are arranged in a grid-like structure.

5. An apparatus according to claim 1, wherein each primary zone forms a respective primary alignment with the related slot, and wherein all respective primary alignments are parallel.

6. An apparatus according to claim 1, wherein the distance between a primary zone and the related slot is less than 20 cm.

7. An apparatus according to claim 1, wherein the distance between two primary zones corresponds to the distance between the related two slots.

8. An apparatus according to claim 1,
wherein the plurality of slots includes at least three slots and
wherein the distances between a respective primary zone and adjacent primary zones are the same.

9. An apparatus according to claim 1, wherein at least one primary graphical information part comprises color-coded information.

10. An apparatus according to claim 1, wherein at least one primary graphical information part comprises information relating to a status of the related slot.

11. An apparatus according to claim 1, wherein at least one primary graphical information part comprises information relating to a sampler held by the related slot.

12. An apparatus according to claim 1, comprising a plurality of intermediate display parts comprising an intermediate display part for each slot, wherein each intermediate display part is configured to display respective intermediate information relating to the respective slot.

13. An apparatus according to claim 12, wherein each intermediate display part is provided such that the distance between the respective intermediate display part and the at least one display area is smaller than the distance between the related slot and the at least one display area, and wherein the distance between each respective intermediate display part and the related slot is less than 10 cm.

14. An apparatus according to claim 12, wherein each intermediate display part comprises an LED.

15. An apparatus according to claim 1, wherein the primary graphical information part displayed at a primary zone comprises pulsating and/or varying intensity visuals.

16. An apparatus according to claim 1, configured to display secondary graphical information at a secondary zone of the at least one display area, wherein the secondary graphical information relates to the slot relating to a selected primary zone.

17. An apparatus according to claim 16, wherein the secondary zone is provided such that the distance between the selected primary zone and the related slot is smaller than the distance between the secondary zone and the related slot.

18. An apparatus according to claim 2, configured to display secondary graphical information at a secondary zone of the at least one display area, wherein the secondary graphical information relates to the slot relating to a selected primary zone, wherein the secondary zone is provided such that the distance between the selected primary zone and the related slot is smaller than the distance between the secondary zone and the related slot, and wherein the secondary zone is provided such that the selected primary zone is between the secondary zone and the proximity point defined by the related slot.

19. An apparatus according to claim 16, wherein the secondary graphical information supplements the related primary graphical information part.

20. An apparatus according to claim 1, wherein the at least one inlet comprises a first inlet configured to withdraw a body fluid sample from a sampler from any of the slots.

21. An apparatus according to claim 20, wherein the sampler bed and/or the individual slots are moveable in relation to the first inlet.

22. An apparatus according to claim 12, wherein the intermediate information displayed by the intermediate display part comprises pulsating and/or varying intensity visuals.

23. A method for analyzing a body fluid sample from a sampler, the method comprising:

receiving a sampler containing a body fluid sample at a slot of a sampler bed comprising a plurality of slots;

withdrawing the body fluid sample from the sampler using an inlet;

providing the withdrawn body fluid sample to an analyzing unit configured to analyze body fluid samples; and displaying graphical information simultaneously within a plurality of primary zones of at least one display area of at least one display unit, wherein the plurality of primary zones comprises a primary zone for each slot, and wherein each of the primary zones individually faces a respective slot, and wherein the graphical information comprises a respective primary graphical information part within each primary zone, and wherein each respective primary graphical information part relates to the respective slot faced by the respective primary zone.

* * * * *